US009518043B2

(12) United States Patent
Bang et al.

(10) Patent No.: US 9,518,043 B2
(45) Date of Patent: Dec. 13, 2016

(54) METHOD FOR PREPARING 1-(4-(4-(3,4-DICHLORO-2-FLUOROPHENYL-AMINO)-7-METHOXYQUINAZOLIN-6-YLOXY)PIPERIDIN-1-YI)PROP-2-EN-1-ONE

(71) Applicant: HANMI PHARM. CO., LTD., Gyeonggi-do (KR)

(72) Inventors: Keuk Chan Bang, Gyeonggi-do (KR); Jae Hyuk Jung, Seoul (KR); Young Ho Moon, Gyeonggi-do (KR)

(73) Assignee: Hanmi Pharm. Co., Ltd., Gyeonggi-do (KR)

( * ) Notice: Subject to any disclaimer, the term of this patent is extended or adjusted under 35 U.S.C. 154(b) by 0 days.

(21) Appl. No.: 14/763,295

(22) PCT Filed: Jan. 27, 2014

(86) PCT No.: PCT/KR2014/000752
§ 371 (c)(1),
(2) Date: Jul. 24, 2015

(87) PCT Pub. No.: WO2014/116070
PCT Pub. Date: Jul. 31, 2014

(65) Prior Publication Data
US 2015/0344458 A1 Dec. 3, 2015

(30) Foreign Application Priority Data
Jan. 28, 2013 (KR) .................. 10-2013-0009282

(51) Int. Cl.
C07D 401/12 (2006.01)
C07D 239/86 (2006.01)
C07D 239/94 (2006.01)
C07D 211/46 (2006.01)

(52) U.S. Cl.
CPC .......... *C07D 401/12* (2013.01); *C07D 211/46* (2013.01); *C07D 239/86* (2013.01); *C07D 239/94* (2013.01)

(58) Field of Classification Search
CPC .................... C07D 401/12; C07D 239/86
USPC ............................................ 544/293
See application file for complete search history.

(56) References Cited

U.S. PATENT DOCUMENTS

| 5,041,580 | A | 8/1991 | Miyamoto et al. |
| 8,188,102 | B2 | 5/2012 | Lee et al. |
| 8,859,767 | B2 * | 10/2014 | Bang ............... A61K 31/517 544/293 |
| 2006/0088592 | A1 | 4/2006 | Choi et al. |
| 2007/0037837 | A1 | 2/2007 | Hennequin et al. |
| 2007/0135463 | A1 | 6/2007 | Himmelsbach et al. |
| 2008/0032996 | A1 | 2/2008 | Mitsuya et al. |
| 2010/0179120 | A1 | 7/2010 | Lee et al. |
| 2013/0071452 | A1 | 3/2013 | Kim et al. |

FOREIGN PATENT DOCUMENTS

| ES | 2342965 T3 | 7/2010 |
| JP | H11349479 A | 12/1999 |
| JP | 2010529115 A | 8/2010 |
| JP | 2010-530890 A | 9/2010 |
| KR | 1019980008219 | 4/1998 |
| KR | 102000048572 | 7/2000 |
| KR | 1020020032612 | 5/2002 |
| KR | 10-2005-0104152 | 11/2005 |
| KR | 1020080107294 | 12/2008 |
| KR | 10-1013319 B1 | 2/2011 |
| RU | 2140782 C1 | 11/1999 |
| TW | 520364 B | 2/2003 |
| TW | 200906414 A | 2/2009 |
| WO | WO-98/13354 A1 | 4/1998 |
| WO | WO-02/18351 A1 | 3/2002 |
| WO | WO-02/18370 A1 | 3/2002 |
| WO | WO-03/82290 A1 | 10/2003 |
| WO | WO-2005/030757 A1 | 4/2005 |
| WO | WO-2005/030765 A1 | 4/2005 |
| WO | WO-2005/033096 A1 | 4/2005 |
| WO | WO-2005/090332 A1 | 9/2005 |
| WO | WO-2007/023073 A2 | 3/2007 |
| WO | WO-2007/118854 A1 | 10/2007 |
| WO | WO-2008/150118 A2 | 12/2008 |
| WO | WO-2009/002826 A2 | 12/2008 |
| WO | WO-2010/123340 A1 | 10/2010 |
| WO | WO-2011/088149 A2 | 7/2011 |
| WO | WO-2011/155793 A2 | 12/2011 |
| WO | WO-2012/169733 A1 | 12/2012 |
| WO | WO-2013/051883 A2 | 4/2013 |

OTHER PUBLICATIONS

Anonymous, "Handbook of Pharmaceutical Excipients", 2006, Pharmaceutical Press, XP002736604, p. 767.
Anonymous, "The Merck Index", 2001, Merck & Co. Inc., XP002736605, p. 5682.
Article as to alginic acid published by Drug Topics (Oct. 2008).
Ballard et al., Inhibitors of epidermal growth factor receptor tyrosine kinase: optimisation of potency and in vivo pharmacokinetics, Bioorg. Med. Chem. Lett., 16(18):4908-12 (2006).
Cha et al., Antitumor activity of HM781-36B, a highly effective pan-H ER inhibitor in erlotinib-resistant NSCLC and other EGFR-dependent cancer models, Int. J. Cancer, 130(10):2445-54 (2012).
Denny, Irreversible inhibitors of the erbB family of protein tyrosine kinases, Pharm. Therapeutics, 83(2-3):253-61 (2002).
Eriksson et al., Synthesis of [11C]/[13C]acrylamides by palladium-mediated carbonylation, Eur. J. Org. Chem., 2007(3):455-61 (2007).
Extended European Search Report, European patent application No. 14743689.3, dated Jun. 7, 2016.
International Preliminary Report on Patentability, International Application No. PCT/KR2014/000752, mailed Jul. 28, 2015.

(Continued)

*Primary Examiner* — Golam M M Shameem
(74) *Attorney, Agent, or Firm* — Marshall, Gerstein & Borun LLP

(57) ABSTRACT

The present invention relates to a novel method for preparing 1-(4-(4-(3,4-dichloro-2-fluorophenylamino)-7-methoxyquinazolin-6-yloxy)piperidin-1-yl)prop-2-en-1-one in a simpler process as compared with conventional methods by allowing 4-(3,4-dichloro-2-fluorophenylamino)-7-methoxyquinazolin-6-ol to react with an N-acyl piperidine derivative in an inert polar protic solvent in the presence of a base.

13 Claims, No Drawings

(56) References Cited

OTHER PUBLICATIONS

International Search Report and Written Opinion, International Application No. PCT/KR2014/000752, mailed May 9, 2014.
Nam et al., Antitumor activity of HM781-36B, an irreversible Pan-HER inhibitor, alone or in combination with cytotoxic chemotherapeutic agents in gastric cancer, Cancer Lett., 302:155-65 (2011).
Pharmaceutical excipients including alginic acid published by International Cenological Codex (Apr. 10, 2010).
Pharmaceutics Manual (the 2nd edition), Namsandang: pp. 83, 84, 110, 120 (1998).
Smaill et al., Tyrosine kinase inhibitors. 15. 4-(Phenylamino)quinazoline and 4-(Phenylamino)pyrido[d]pyrimidine Acrylamides as Irreversible inhibitors of the ATP binding site of the epidermal growth factor receptor, J. Med. Chem., 42:1803-15 (1999).
Thoma et al., Enteric coated hard gelatin capsules, Department of Pharmaceutical Technology, Ludwig Maximillian University, 8000 Munich 2, Germany, published in 2000.

* cited by examiner

METHOD FOR PREPARING 1-(4-(4-(3,4-DICHLORO-2-FLUOROPHENYL-AMINO)-7-METHOXYQUINAZOLIN-6-YLOXY)PIPERIDIN-1-YL)PROP-2-EN-1-ONE

CROSS-REFERENCE TO RELATED PATENT APPLICATIONS

This application is a U.S. National Phase Application under 35 U.S.C. §371 of International Patent Application No. PCT/KR2014/000752, filed Jan. 27, 2014, and claims the priority of KR 10-2013-0009282, filed Jan. 28, 2013, all of which are incorporated by reference in their entireties. The International Application was published on Jul. 31, 2014 as International Publication No. WO 2014/116070 A1.

FIELD OF THE INVENTION

The present invention relates to a novel method for preparing 1-(4-(4-(3,4-dichloro-2-fluorophenylamino)-7-methoxyquinazolin-6-yloxy)piperidin-1-yl)prop-2-en-1-one, a free base form of a specific drug (hydrochloride form) which can selectively and effectively inhibit drug resistance induced by the growth of cancer cells and tyrosine kinase mutations. By the inventive method the target compound can be prepared in a much simpler process as compared with conventional methods.

BACKGROUND OF THE INVENTION 1-(4-(4-(3,4-dichloro-2-fluorophenylamino)-7-methoxy-quinazolin-6-yloxy)piperidin-1-yl)prop-2-en-1-one hydrochloride, as represented by formula (IV) below, is known to have anti-proliferative activities such as anti-cancer activities, and it is considered as an important drug that can selectively and effectively inhibit drug resistance which is induced by cancer cell growth and tyrosine kinase mutations. The free base form of the compound of formula (IV), i.e., 1-(4-(4-(3,4-dichloro-2-fluorophenylamino)-7-methoxyquinazolin-6-yloxy)piperidin-1-yl)prop-2-en-1-one, as represented by formula (I) below, is also known as CAS Registry No. 1092364-38-9.

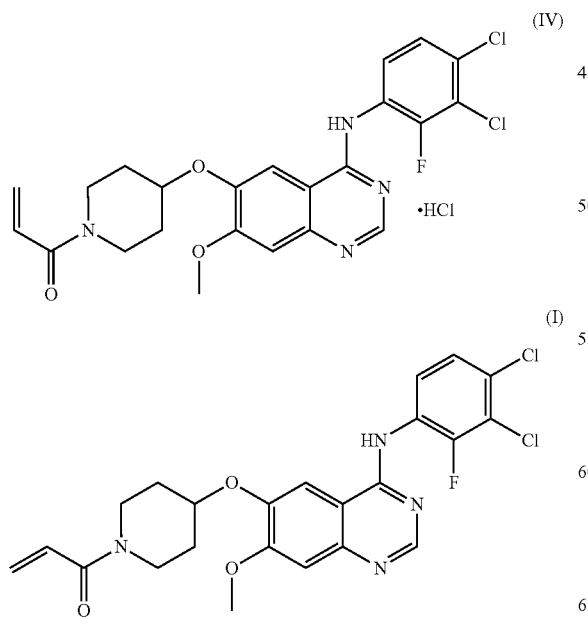

The compound of formula (I) above may be prepared by the method disclosed in KR Patent No. 1013319, and the detailed reaction process is described in Reaction Scheme 1 below. The compound of formula (I) prepared by Reaction Scheme (I) below may be reacted with hydrochloric acid to yield a hydrochloride salt thereof, i.e., the compound of formula (IV):

Reaction Scheme 1

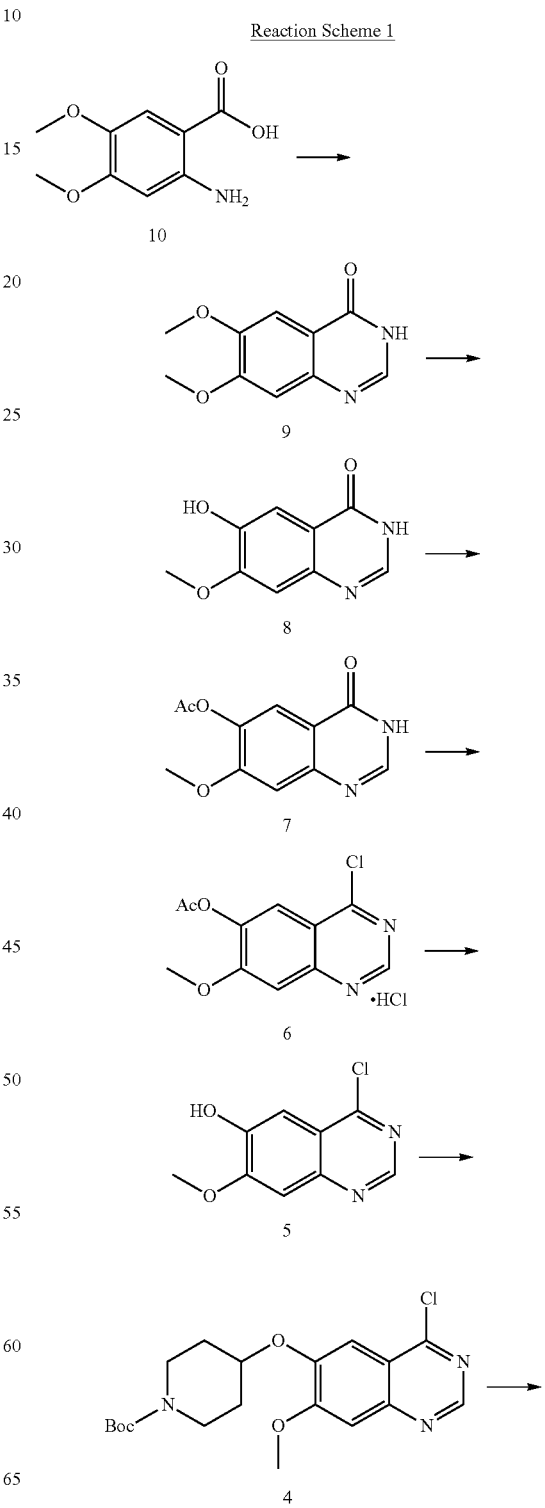

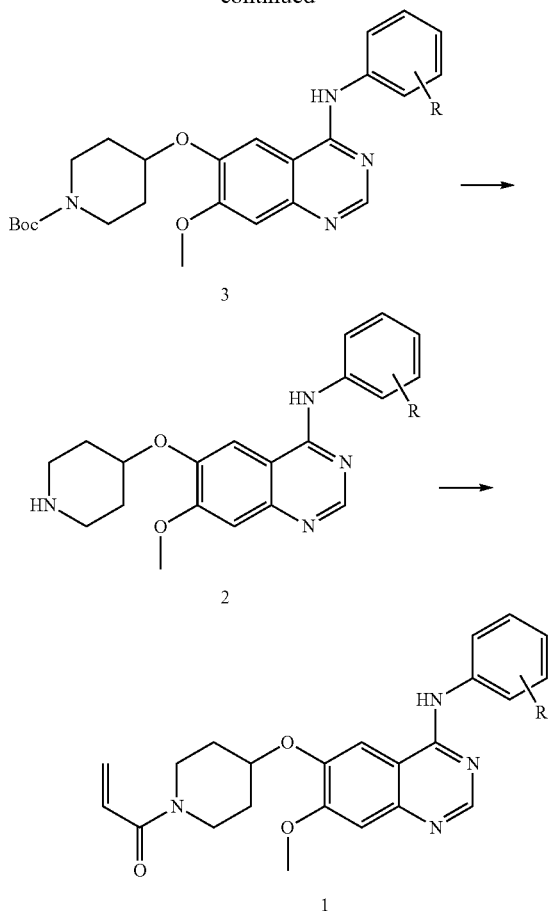

wherein R is halogen.

According to the preparation method as described in Reaction Scheme 1 above, compound 10 is subjected to a condensation reaction with formamidine hydrochloride at a high temperature, e.g., 210° C., to yield compound 9, which is then allowed to react with L-methionine in an organic acid such as methylsulfonic acid, whereby the methyl group at the C-6 position of compound 9 is removed to obtain compound 8.

Subsequently, compound 8 is subjected to a protection reaction in anhydrous acetic acid and a base such as pyridine to produce compound 7, which is then subjected to a reaction with inorganic acids such as thionyl chloride, phosphorus oxychloride and the like in the presence of a catalytic amount of N,N-dimethylformamide under a reflux condition to obtain compound 6 in a hydrochloride form.

Compound 6 thus obtained is subjected to a deprotection reaction by stirring in an alcohol solution containing ammonia (e.g., 7N ammonia methanol solution) to produce compound 5. Compound 5 is subjected to a Mitsunobu reaction with tert-butyl 4-hydroxypiperidine-1-carboxylate compound to yield compound 4, which is then subjected to a substitution reaction with aniline in an organic solvent such as 2-propanol or acetonitrile to obtain compound 3. Compound 3 is subjected to a reaction with an organic acid such as trifluoroacetic acid or an inorganic acid such as strong hydrochloric acid in an organic solvent such as dichloromethane, whereby the t-butoxycarbonyl group is deprotected to obtain compound 2. In the Mitsunobu reaction above, diisopropyl azodicarboxylate, diethyl azodicarboxylate or di-t-butyl azodicarboxylate, and triphenylphosphine may be used.

Compound 1, i.e., the compound of formula (I) of the present invention, is prepared by subjecting compound 2 thus obtained to an acylation reaction with acryloyl chloride in a mixture of water and an organic solvent such as tetrahydrofuran and the like, or in dichloromethane in the presence of an inorganic base such as sodium bicarbonate or an organic base such as pyridine or triethylamine. Alternatively, compound 2 is subjected to a condensation reaction with acrylic acid by using a coupling agent, e.g., 1-ethyl-3-(3-dimethylaminopropyl)-carbodiimide (EDC) or 2-(1H-7-azabenzotriazol-1-yl)-1,1,3,3-tetramethyluronium hexafluorophosphate methanaminium (HATU).

In accordance with the above-described method, however, the step for preparing compound 9 may be hazardous because this step is conducted at a high temperature without a solvent, and the reaction may not proceed uniformly. Also, an excessive amount of thionyl chloride is used in the step for preparing compound 5, rendering the subsequent steps difficult. Therefore, this method is not suitable for commercialization.

The most notable drawback to this method for preparing compound 1 is that the yield of the acrylization reaction is very low, e.g., 13%, and also the reaction is accompanied by a number of side reactions, and thus, it requires a purification process by using column chromatography. Also, in the case where compound 3 is prepared by the Mitsunobu reaction, various by-products may be formed, which necessitate a purification step by using column chromatography that requires expensive silica gel and an excessive amount of mobile phase solvents. Therefore, this method is not feasible for commercialization.

Accordingly, the present inventors have endeavored to develop a novel method for preparing the compound of formula (I) in high purity and high yield, which is economical and feasible for commercialization as well.

SUMMARY OF THE INVENTION

Therefore, it is an object of the present invention to provide a novel and simple method for preparing 1-(4-(4-(3,4-dichloro-2-fluorophenylamino)-7-methoxyquinazolin-6-yloxy)piperidin-1-yl)prop-2-en-1-one.

In accordance with one aspect of the present invention, there is provided a method for preparing the compound of formula (I), which comprises the step of allowing the compound of formula (II) to react with the compound of formula (III) in an inert polar protic solvent in the presence of a base:

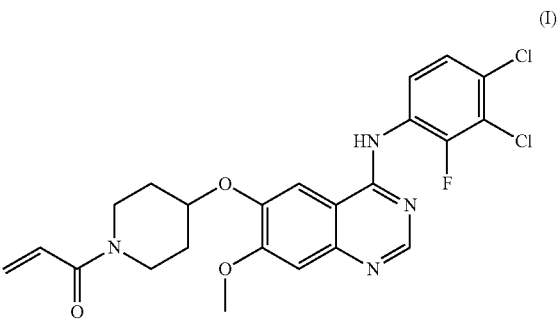

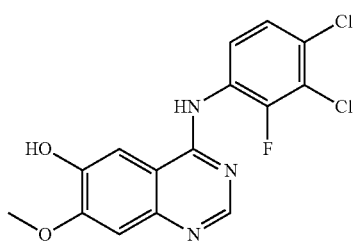

(II)

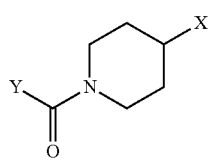

(III)

wherein X is tosyloxy (OTs), mesyloxy (OMs), trifluoromethane sulfonate, fluorosulfonate or halogen; and Y is ethenyl or halogenoethyl.

DETAILED DESCRIPTION OF THE INVENTION

According to the method of the present invention, the compound of formula (I), i.e., 1-(4-(4-(3,4-dichloro-2-fluorophenylamino)-7-methoxyquinazolin-6-yloxy)piperidin-1-yl)prop-2-en-1-one, can be prepared by allowing the compound of formula (II), i.e., 4-(3,4-dichloro-2-fluorophenylamino)-7-methoxyquinazolin-6-ol, to react with the compound of formula (III) in an inert polar protic solvent in the presence of a base. This mechanism is described in Reaction Scheme 2 below:

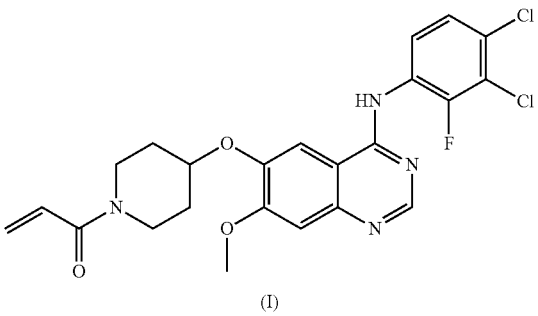

(I)

wherein X and Y are the same as defined above.

Particular examples of the inert polar protic solvent used in the above reaction include N,N-dimethylformamide, N,N-dimethylacetamide, N-methylpyrrolidin-2-one, dimethyl sulfoxide and a mixture thereof.

Particular examples of the base used in the above reaction is alkali metal carbonates such as sodium bicarbonate, potassium carbonate, cesium carbonate and a mixture thereof. Preferably, the base is used in an amount of 1 to 5 mole equivalents based on 1 mole equivalent of the compound of formula (II).

The above reaction may be conducted at a temperature of 60° C. to 100° C., preferably 70° C. to 90° C., more preferably 70° C. to 80° C.

The compound of formula (II), which is used as a starting material in the present invention, can be prepared by the following steps (see Reaction Scheme 3 below):

(i) subjecting a compound of formula (VII) to a reaction with a halogenating agent in the presence of an organic base to produce the compound of formula (VI), which is then subjected to a reaction with a compound of formula (VIII) to obtain the compound of formula (V), i.e., 4-(3,4-dichloro-2-fluorophenylamino)-7-methoxyquinazolin-6-yl acetate; and (ii) subjecting the compound of formula (V) to a reaction with an ammonia solution in a polar protic solvent.

Reaction Scheme 2

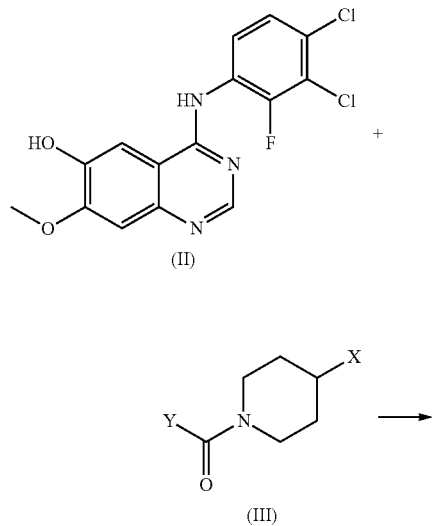

Reaction Scheme 3

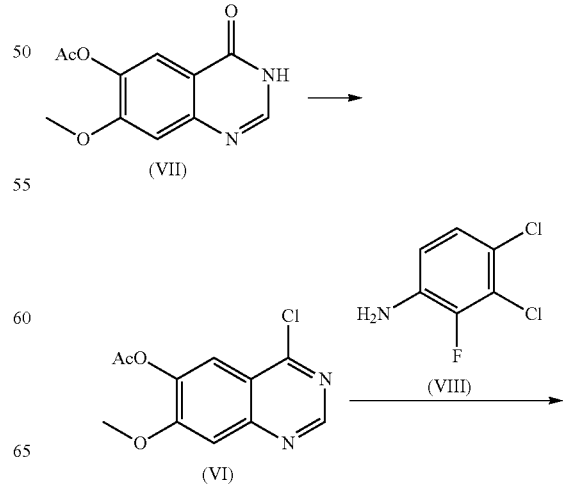

(V)

(II)

Particular examples of the organic base used in Step (i) above include diisopropylamine, triethylamine, diisopropylethylamine, diethylamine, pyridine, 4-dimethylpyridine, morpholine and a mixture thereof. Particular examples of the halogenating agent include thionyl chloride, phosphorus oxychloride and a mixture thereof. The above reaction may be conducted at 50° C. to 150° C., preferably 60° C. to 90° C., more preferably at about 75° C. In this step, the compound of formula (VI) is prepared in the form of a solution containing it in an organic solvent, rather than an isolated form. Subsequently, the compound of formula (VI) contained in the organic solvent is allowed to react with the compound of formula (VIII) to obtain the compound of formula (V), i.e., 4-(3,4-dichloro-2-fluorophenylamino)-7-methoxyquinazolin-6-yl acetate.

The compound of formula (VII), which is used as a starting material of the above reaction, can be prepared by the method disclosed in Korean Patent No. 1013319.

In the subsequent step (ii), the compound of formula (V) prepared in the previous step (i) is allowed to react with an ammonia solution or ammonia gas in a polar protic solvent (e.g., methanol, ethanol, propanol and a mixture thereof) at a temperature of 0° C. to 40° C., preferably 10° C. to 30° C., more preferably at about 25° C., to obtain 4-(3,4-dichloro-2-fluorophenylamino)-7-methoxyquinazolin-6-ol of formula (II).

Also, the compound of formula (III), which is used as a starting material of the present invention, can be prepared by allowing the compound of formula (IX) or its salt to react with the compound of formula (X) in the presence of a base or an amide coupling agent (see Reaction Scheme 4 below):

Reaction Scheme 4

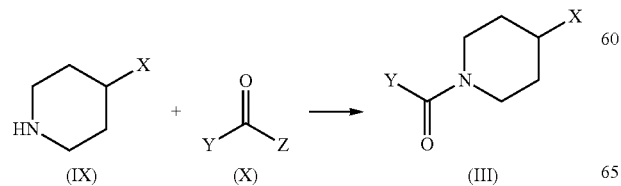

wherein X and Y are the same as defined above; and Z is halogen or hydroxyl.

The above reaction can be conducted in an organic solvent such as tetrahydrofuran, ethyl acetate, acetone, 1,4-dioxane, acetonitrile, dichloromethane, carbon tetrachloride, chloroform, N,N-dimethyl formamide or dimethylsulfoxide, or in a mixture of an organic solvent and water.

Particular examples of the base include an inorganic base such as sodium carbonate, sodium bicarbonate, calcium carbonate, potassium carbonate, sodium hydroxide, potassium hydroxide and cesium carbonate, an organic base such as diisopropylamine, triethylamine, diisopropylethylamine and diethylamine, and a mixture thereof. Particular examples of the amide coupling agent include 1-ethyl-3-(3-dimethylaminopropyl)carbodiimide, hydroxybenzotriazole, O-(7-azabenzotriazol-1-yl)-N,N,N',N'-tetramethyluronium hexafluorophosphate, N,N'-dicyclohexylcarboimide, 1-hydroxy-7-azabenzotriazole, N-N'-diisopropylcarboimide, (benzotriazol-1-yloxy)tris(dimethylamino)phosphonium hexafluorophosphate and a mixture thereof. The base or amide coupling agent may be used in an amount of 3 to 5 mole equivalents based on 1 mole equivalent of the compound of formula (IX) or a salt thereof.

The salt of the compound of formula (IX) above is preferably a hydrochloride salt (2HCl salt) or a hydrobromide salt (2HBr salt). The above reaction may be conducted at a temperature of −30° C. to 30° C., preferably about 0° C. to room temperature, by stirring for a suitable period of time.

In accordance with the method of the present invention, the target compound of formula (I), 1-(4-(4-(3,4-dichloro-2-fluorophenylamino)-7-methoxyquinazolin-6-yloxy)piperidin-1-yl)prop-2-en-1-one, can be prepared in high purity and high yield by a simple method.

Moreover, 1-(4-(4-(3,4-dichloro-2-fluorophenylamino)-7-methoxyquinazolin-6-yloxy)piperidin-1-yl)prop-2-en-1-one hydrochloride, which can selectively and effectively inhibit drug resistance induced by the growth of cancer cells and tyrosine kinase mutations, can be prepared by allowing the compound of formula (I) to react with hydrochloric acid in an organic solvent (e.g., methanol, ethanol, propanol, isopropanol, butanol, ethyl acetate, acetone, tetrahydrofuran, acetonitrile, 1,4-dioxane and a mixture thereof) at a temperature of 0° C. to 60° C., preferably 10° C. to 40° C., more preferably at about 25° C.

Hereinafter, the present invention is described more specifically by the following Examples, but these are provided only for illustration purposes, and the present invention is not limited thereto.

Preparation Example 1

Preparation of 4-(3,4-dichloro-2-fluorophenylamino)-7-methoxyquinazolin-6-ol, the Compound of Formula (II)

Step (i): Preparation of 4-(3,4-dichloro-2-fluorophenylamino)-7-methoxyquinazolin-6-yl acetate, the compound of formula (V)

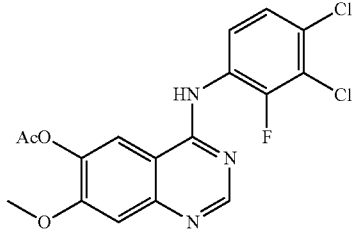 [SMILES: COc1cc2ncnc(Nc3ccc(Cl)c(Cl)c3F)c2cc1OC(C)=O]

7-methoxy-4-oxo-3,4-dihydroquinazolin-6-yl acetate (100 g) was added to toluene (850 mL) and N,N-diisopropylethylamine (82.5 mL). Phosphorus oxychloride (100 mL) was added thereto over 20 minutes at 75° C., followed by stirring for 3 hours. Toluene (450 mL) and 3,4-dichloro-2-fluoroaniline (84.6 g) were added to the resulting mixture, followed by stirring for 2 hours. Upon completion of the reaction, the resulting mixture was cooled to 25° C., and the solid thus obtained was filtered under a reduced pressure and washed with toluene (400 mL). Isopropanol (1,000 mL) was added to the solid, and the resulting mixture was stirred for 2 hours. The solid thus obtained was filtered and washed with isopropanol (400 mL), and then was dried at 40° C. in an oven to obtain the target compound (143 g, yield: 83%).

$^1$H-NMR (DMSO-$d_6$, 300 MHz, ppm) δ8.92 (s, 1H), 8.76 (s, 1H), 7.69-7.57 (m, 3H), 4.01 (s, 3H), 2.38 (s, 3H).

Step (ii): Preparation of 4-(3,4-dichloro-2-fluorophenylamino)-7-methoxyquinazolin-6-ol, the compound of formula (II)

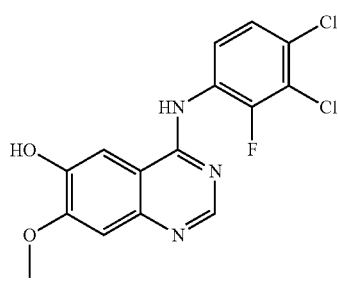 [SMILES: COc1cc2ncnc(Nc3ccc(Cl)c(Cl)c3F)c2cc1O]

4-(3,4-dichloro-2-fluorophenylamino)-7-methoxyquinazolin-6-yl acetate (100 g) prepared in step (i) was admixed with methanol (1,000 mL). The mixture was cooled to 10 to 15° C., added with an ammonia solution (460 g), and stirred for 3 hours at 25° C. The solid thus obtained was filtered and washed with a mixed solvent of methanol (200 mL) and water (200 mL). The resulting solid was dried at 40° C. in an oven to obtain the target compound (74 g, yield: 83%).

$^1$H-NMR (DMSO-$d_6$, 300 MHz, ppm) δ9.57 (br, 2H), 8.35 (s, 1H), 7.68 (s, 1H), 7.61-7.52 (m, 2H), 7.21 (s, 1H), 3.97 (s, 3H).

Example 1

Preparation of 1-(4-(4-(3,4-dichloro-2-fluorophenylamino)-7-methoxyquinazolin-6-yloxy)piperidin-1-yl)prop-2-en-1-one, the Compound of Formula (I)

Step (1-1): Preparation of 1-acryloylpiperidin-4-yl 4-methylbenzenesulfonate, the compound of formula (III)

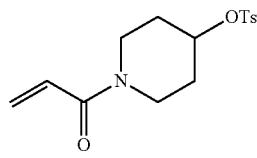 [SMILES: C=CC(=O)N1CCC(OS(=O)(=O)c2ccc(C)cc2)CC1]

Piperidin-4-yl 4-methylbenzenesulfonate hydrochloride (200 g, 685 mmol), tetrahydrofuran (THF, 1.6 L) and NaHCO$_3$ (172 g, 2047 mmol) were added to water (2 L), and the mixture was cooled to 0° C. A solution prepared by adding acryloyl chloride (56 mL, 519 mmol) to THF (0.4 L) was added thereto over 30 minutes, followed by stirring for 1 hour. Upon completion of the reaction, MeOH (0.4 L) was added thereto for quenching. The solution was extracted with ethyl ester (2 L), and washed with water (2 L). The organic layer was separated, distilled under a reduced pressure, and the residue thus obtained was recrystallized from dichloromethane-hexane to obtain the target compound (174 g, yield: 82%).

$^1$H-NMR (300 MHz, DMSO-$d_6$) δ7.82 (d, 2H), 7.48 (d, 2H), 6.80-6.71 (m, 1H), 6.10-6.03 (m, 1H), 5.67-5.62 (m, 1H), 4.76-4.71 (m, 1H), 3.70-3.68 (m, 2H), 3.43-3.31 (m, 2H), 2.42 (s, 3H), 1.73 (m, 2H), 1.52 (m, 2H).

Step (1-2): Preparation of 1-(4-(4-(3,4-dichloro-2-fluorophenylamino)-7-methoxyquinazolin-6-yloxy)piperidin-1-yl)prop-2-en-1-one the compound of formula (I)

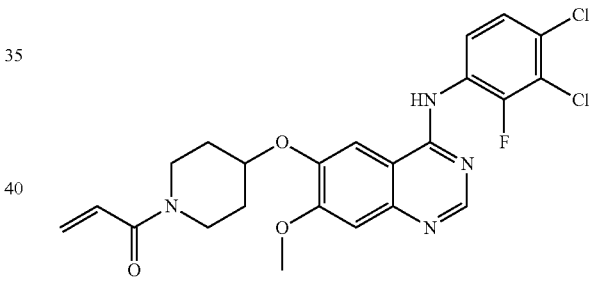

4-(3,4-dichloro-2-fluorophenylamino)-7-methoxyquinazolin-6-ol (12 g, 34 mmol) prepared in Preparation Example 1, 1-acryloylpiperidin-4-yl 4-methylbenzenesulfonate (16 g, 51 mmol) prepared in step (1-1), K$_2$CO$_3$ (9.4 g, 68 mmol) and dimethylacetamide (DMAc, 300 mL) were admixed. The reaction temperature was raised to 70° C., and the mixture was stirred for 24 hours. Upon completion of the reaction, the mixture was cooled down to room temperature, extracted with ethyl ester (300 mL), and then washed with water (300 mL). The organic layer was separated, and distilled under a reduced pressure. The residue thus obtained was solidified by adding ethyl ester, filtered, and dried to obtain the target compound (12.8 g, yield: 77%).

$^1$H-NMR (300 MHz, DMSO-$d_6$) δ9.65 (bs, 1H), 8.40 (s, 1H), 7.88 (s, 1H), 7.64-7.56 (m, 2H), 7.24 (s, 1H), 6.89-6.80 (m, 1H), 6.15-6.08 (m, 1H), 5.70-5.66 (m, 1H), 4.78 (m, 1H), 3.94 (s, 3H), 3.87 (m, 2H), 3.48 (m, 2H), 2.03 (m, 2H), 1.70 (m, 1H).

Example 2

Preparation of 1-(4-(4-(3,4-dichloro-2-fluorophenylamino)-7-methoxyquinazolin-6-yloxy)piperidin-1-yl)prop-2-en-1-one, the Compound of Formula (I)

Step (2-1): Preparation of 1-(3-chloropropanoyl)piperidin-4-yl 4-methylbenzenesulfonate, the compound of formula (III)

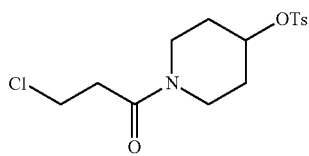 [SMILES: Cc1ccc(S(=O)(=O)OC2CCN(C(=O)CCCl)CC2)cc1]

Piperidin-4-yl 4-methylbenzensulfonate hydrochloride (20 g, 68 mmol) and dichloromethane (200 mL) were admixed and the mixture was cooled down to 0° C. Triethylamine (29 mL, 205 mmol) and 3-chloropropionyl chloride (7.9 mL, 82 mmol) were added thereto, followed by stirring for 16 hours at room temperature. Upon completion of the reaction, the reaction mixture was extracted with ethyl ester (200 mL), and washed with water (200 mL). The organic layer was separated, distilled under a reduced pressure, and the residue thus obtained was purified to obtain the target compound (18 g, yield: 76%).

$^1$H-NMR (300 MHz, CDCl$_3$) δ7.80 (d, 2H), 4.76-4.72 (m, 1H), 3.80 (t, 2H), 3.64-3.57 (m, 3H), 3.40 (m, 1H), 2.77 (t, 2H), 2.46 (s, 3H), 1.85-1.70 (m, 4H).

Step (2-2): Preparation of 1-(4-(4-(3,4-dichloro-2-fluorophenylamino)-7-methoxyquinazolin-6-yloxy)piperidin-1-yl)prop-2-en-1-one, the compound of formula (I)

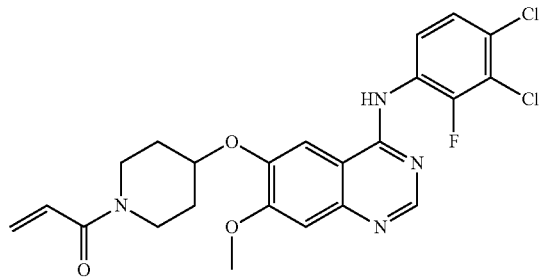 [SMILES: C=CC(=O)N1CCC(Oc2cc3c(Nc4ccc(Cl)c(Cl)c4F)ncnc3cc2OC)CC1]

The procedure of Step (1-2) of Example 1 was repeated, except 1-(3-chloropropanoyl)piperidin-4-yl 4-methylbenzenesulfonate (13 g, 35 mmol) prepared in step (2-1) above was used instead of 1-acryloylpiperidin-4-yl 4-methylbenzenesulfonate (16 g, 51 mmol) prepared in step (1-1), to obtain the target compound (7.4 g, yield: 58%).

$^1$H-NMR (300 MHz, DMSO-d$_6$) δ9.65 (bs, 1H), 8.40 (s, 1H), 7.88 (s, 1H), 7.64-7.56 (m, 2H), 7.24 (s, 1H), 6.89-6.80 (m, 1H), 6.15-6.08 (m, 1H), 5.70-5.66 (m, 1H), 4.78 (m, 1H), 3.94 (s, 3H), 3.87 (m, 2H), 3.48 (m, 2H), 2.03 (m, 2H), 1.70 (m, 1H).

What is claimed is:

1. A method for preparing the compound of formula (I), which comprises the step of allowing the compound of formula (II) to react with the compound of formula (III) in an inert polar protic solvent in the presence of a base:

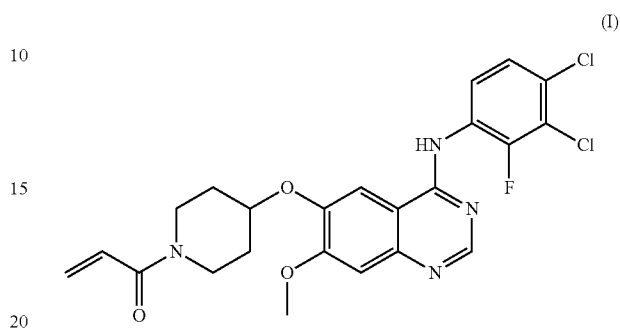

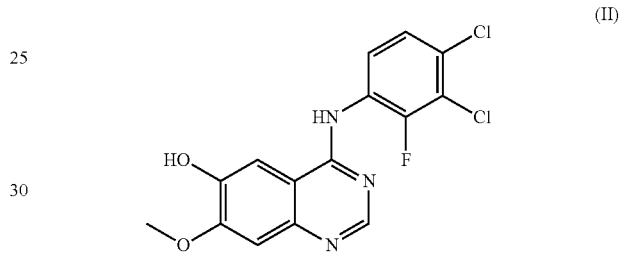

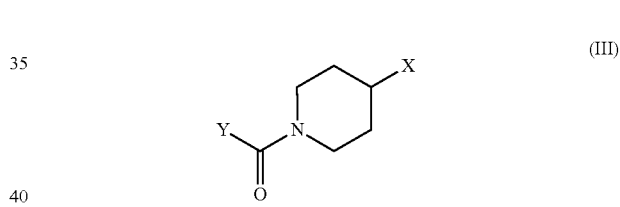

wherein X is tosyloxy (OTs), mesyloxy (OMs), trifluoromethane sulfonate, fluorosulfonate or halogen; and Y is ethenyl or halogenoethyl.

2. The method of claim 1, wherein the inert polar protic solvent is selected from the group consisting of N,N-dimethylformamide, N,N-dimethylacetamide, N-methylpyrrolidin-2-one, dimethyl sulfoxide and a mixture thereof.

3. The method of claim 1, wherein the base is an alkali metal carbonate selected from the group consisting of sodium bicarbonate, potassium carbonate, cesium carbonate and a mixture thereof.

4. The method of claim 1, wherein the base is used in an amount of 1 to 5 mole equivalents based on 1 mole equivalent of the compound of formula (II).

5. The method of claim 1, wherein the compound of formula (II) is prepared by (i) subjecting a compound of formula (VII) to a reaction with a halogenating agent in the presence of an organic base to produce the compound of formula (VI), which is then subjected to a reaction with a compound of formula (VIII) to obtain the compound of formula (V); and (ii) subjecting the compound of formula (V) to a reaction with an ammonia solution in a polar protic solvent:

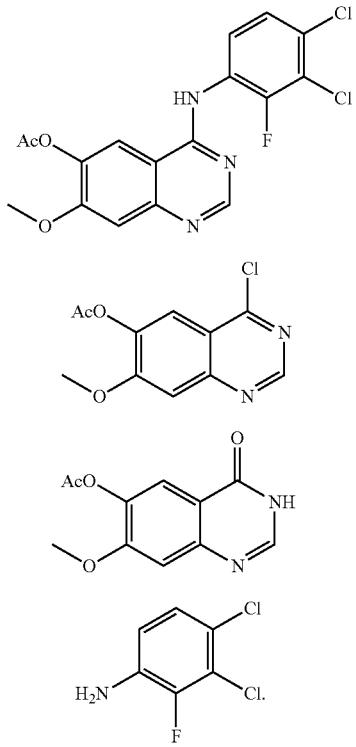

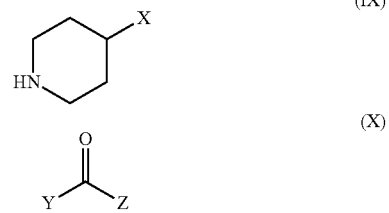

6. The method of claim 5, wherein the organic base is selected from the group consisting of diisopropylamine, triethylamine, diisopropylethylamine, diethylamine, pyridine, 4-dimethylpyridine, morpholine and a mixture thereof.

7. The method of claim 5, wherein the halogenating agent is selected from the group consisting of thionyl chloride, phosphorus oxychloride and a mixture thereof.

8. The method of claim 5, wherein the polar protic solvent is selected from the group consisting of methanol, ethanol, propanol and a mixture thereof.

9. The method of claim 1, wherein the compound of formula (III) is prepared by allowing the compound of formula (IX) or its salt to react with the compound of formula (X) in the presence of a base or an amide coupling agent:

wherein X and Y are the same as defined in claim 1; and Z is halogen or hydroxyl.

10. The method of claim 9, wherein the reaction between the compound of formula (IX) or its salt and the compound of formula (X) is conducted in an organic solvent or a mixture of an organic solvent and water; and the organic solvent is tetrahydrofuran, ethyl acetate, acetone, 1,4-dioxane, acetonitrile, dichloromethane, carbon tetrachloride, chloroform, N,N-dimethyl formamide or dimethylsulfoxide.

11. The method of claim 9, wherein the base used in the reaction between the compound of formula (IX) or its salt and the compound of formula (X) is selected from the group consisting of sodium carbonate, sodium bicarbonate, calcium carbonate, potassium carbonate, sodium hydroxide, potassium hydroxide, cesium carbonate, diisopropylamine, triethylamine, diisopropylethylamine, diethylamine, and a mixture thereof.

12. The method of claim 9, wherein the amide coupling agent is selected from the group 1-ethyl-3-(3-dimethylaminopropyl)carbodiimide, hydroxybenzotriazole, O-(7-azabenzotriazol-1-yl)-N,N,N',N'-tetramethyluronium hexafluorophosphate, N,N'-dicyclohexylcarboimide, 1-hydroxy-7-azabenzotriazole, N-N'-diisopropylcarboimide, (benzotriazol-1-yloxy)tris(dimethylamino)phosphonium hexafluorophosphate and a mixture thereof.

13. The method of claim 9, wherein the salt of the compound of formula (IX) is a hydrochloride or hydrobromide salt.

* * * * *